United States Patent [19]
Truocchio

[11] Patent Number: 5,217,372
[45] Date of Patent: Jun. 8, 1993

[54] DENTISTRY PRACTICE

[76] Inventor: Michael A. Truocchio, 180 Oakfield Ave., Dix Hills, N.Y. 11746-6305

[21] Appl. No.: 946,081

[22] Filed: Sep. 17, 1992

[51] Int. Cl.⁵ ............................................. A61C 5/00
[52] U.S. Cl. .................................... 433/215; 433/229
[58] Field of Search ................ 433/77, 114, 215, 216, 433/229

[56] References Cited

U.S. PATENT DOCUMENTS

| | | | |
|---|---|---|---|
| 5,071,346 | 12/1991 | Domaas | 433/77 |
| 5,127,830 | 7/1992 | Sheridan et al. | 433/77 |
| 5,161,970 | 11/1992 | Baskas | 433/77 |
| 5,172,810 | 12/1992 | Brewer | 433/77 X |

Primary Examiner—Robert P. Swiatek
Assistant Examiner—Nicholas D. Lucchesi

[57] ABSTRACT

A dentistry practice or method requiring a patient's possession of dental drill components, i.e. drill burr, handset or drill burr attaching means, etc., which are unavoidably in danger of HIV virus contamination during typical use, and the relinquishing of this possession to the dentist preparatory to the use thereof, thereby totally obviating any inter-patient contamination of these dental drill components that could transmit the HIV virus resulting in AIDS.

1 Claim, 1 Drawing Sheet

DENTISTRY PRACTICE

BACKGROUND OF THE INVENTION

The present relates to improvements in dentistry practice wherein, more particularly, the improvements render totally safe a typical dental tooth-drilling procedure in regard to transmitting the HIV virus resulting in AIDS.

The high risk of contracting AIDS by a dental patient is well understood because it is almost unavoidable that, during a typical tooth-drilling procedure, the blood of the patient will be present in the patient's mouth and for the drill components, because of their proximity to the patient's mouth, to become infused, by splattering or otherwise, with drops or other small quantities of the patient's blood. Accordingly, all advanced sterilizing techniques, including steam autoclaving, are utilized on the drill components in between sequential uses. This is mistakenly believed to either solve the problem, or to be the best available solution.

Broadly, it is an object of the present invention to provide a safe tooth-drilling procedure overcoming the foregoing and other shortcomings of the prior art. More particularly, it is an object to obviate the transmission of the HIV virus among dental patients of a typical practicing dentist, who will usually typically have 200 patients, using the within inventive method, as all is explained and described in greater detail subsequently herein.

Underlying the method of the present invention is the recognition that all known current methods of sterilizing and preparing dental drill components, e.g. a drill burr, are inadequate to remove all fluids which might contain the HIV virus which results in AIDS. It has been determined, for example, that even after autoclaving there is still some residual fluid, particularly in the crevices of the burrs. These residual fluids can contain the HIV virus, and thus inadvertently transmit this virus from one patient to a subsequent patient exposed to the dental drill components. The consequences of this contamination spreading the HIV virus which results in AIDS is effectively obviated by confining the use of the dental drill components to a patient or a patient's family group in which the HIV virus is non-existent and, therefore, incapable of being transmitted.

The description of the invention which follows, together with the accompanying drawings should not be construed as limiting the invention to the method using the dental drill components shown and described, because those skilled in the art to which this invention appertains will be able to devise other forms thereof within the ambit of the appended claims.

DETAILED DESCRIPTION OF THE INVENTION

Figure 1:
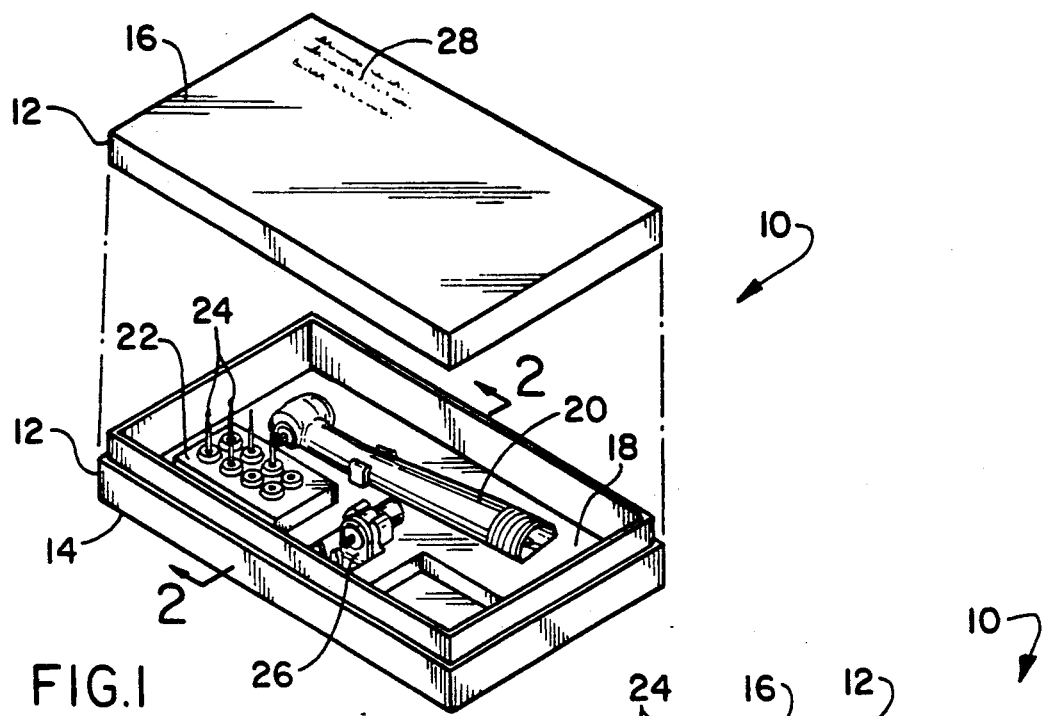
FIG. 1 is a prospective view of a storage and transmittal container with dental drill components for practicing the within inventive method.
Figure 2:
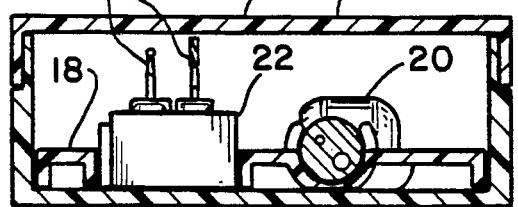
FIG. 2 is a cross-sectional view as taken along line 2—2 of FIG. 1, but showing the cover for the container in its place as a closure.
Figure 3:
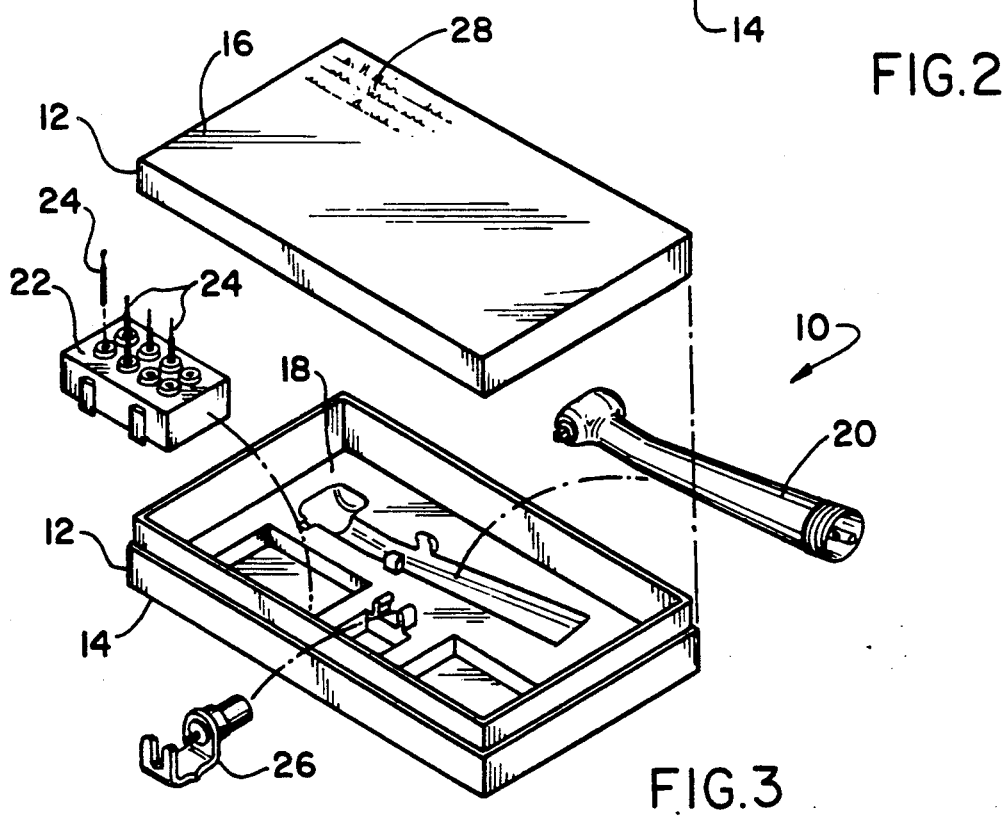
FIG. 3 is a view similar to FIG. 1 of the container, but showing the components removed therefrom.

Illustrated in the drawings is a contemplated what might aptly be called a dental kit, designated 10, consisting in its preferred form of a simple container box 12 having a base 14, a cover 16, and a removable tray insert 18. Insert 18 will be understood to be constructed and shaped in an appropriate manner for receiving therein for storage and transmittal a dental drill burr support 20, also known in trade parlance as a handpiece, one or possibly two well understood and commercially available burr cleaning units 22 which, as is custom in the trade, is provided with an array of dental burrs 24, and also a commercially available well understood so-called burr ejection tool 26. Tray 18 is removably inserted in the base 14 to facilitate for cleaning purposes the dental drill components just noted.

When the dental drill components 20, 24 and 26 are not in use, as is the case between dental visits, the kit 10 is intended, in accordance with the present invention, to be used for the convenient storage at home by the patient for whose dental use the components will be used. The possession by the patient can be on a lease basis, or as outright owner. In either case it is, of course, contemplated that the dental kit with the stored components therein will be maintained under sanitary and reasonably sterile conditions. When the user of the kit 10, or a member of the user's family or of a group known to be at a low risk for HIV infection, is scheduled to see the dentist he/she will bring the kit 10 for use during the dental visit. In this regard, it will, of course, be understood that the dental drill components of kit 10 are selected to be compatible with the dentist's drill equipment. A dental drill recommended for use in practicing the within inventive method is commercially available from Henry Schein, Inc. of Port Washington, N.Y.

At the dentist's office, and again in accordance with the AIDS-obviating method of the present invention, the patient will relinquish possession of the kit 10 to the dentist or the dentist's assistant for conventional cleaning and sterilization, which typically takes 10 to 15 minutes for the cleaning of the drill burr support 20, burrs 24 and burr ejection tool 26, and possibly even including the burr cleaning unit 22, preparatory for subsequent home use. The sterilized dental drill components 20, 24 and 26 are then used in a well-understood manner in a dental tooth-drilling procedure. From what is already described it should be obvious that the possession by the patient, relinquished only to the dentist, assures that there occurs only the exclusive use of the dental drill components 20, 24 and 26 in relation to the particular patient. After use, arrangements will be made for the dental assistant, or whoever is assigned that task, to clean the components 20, 24 and 26 in an appropriate manner and to relinquish the possession thereof to the patient for replacement in the kit 10.

For completeness' sake, it is, of course, noted that worn and replaceable parts or components can be supplied as needed. Also, while in storage, burrs 24 can be further protected with a provided burr sheath (not shown). Kits, such as exemplified by kit 10 hereof and the components therein, may be registered and inscribed with suitable indicia 28 to minimize the possibility of use for patients outside of the exclusive use intended.

Underlying the method of the present invention is the recognition that all known current methods of sterilizing and preparing dental drill components, and specifically components 20, 24 and 26 previously described, are inadequate to remove all fluids which might contain the HIV virus which results in AIDS. It has been demonstrated, for example, that even after autoclaving there is still some residual fluid particularly in the crevices of the burrs. These residual fluids can contain the HIV virus, and thus inadvertently transmit this virus from one patient to a subsequent patient exposed to the dental drill components, 20, 24 and 26. The high risk of contracting AIDS is well understood because it is almost unavoidable during a typical tooth-drilling procedure for the blood of a patient to be present in the patient's mouth and for the drill components 20, 24 and 26, because of their proximity to the patient's mouth, to become infused by splattering or otherwise, with drops or other small quantities of the patient's blood. The significant utility of the within inventive method is the recognition that, while the contamination of the drill components 20, 24 and 26 cannot be prevented, the consequences of this contamination spreading the HIV virus which results in AIDS can be obviated by confining the use of the dental drill components 20, 24 and 26 to a patient or a patient's family group in which the HIV virus is non-existent and, therefore, incapable of being transmitted.

While the within inventive method of exclusive use of dental drill components, and specifically the components referred to as herein shown and disclosed in detail, is fully capable of attaining the objects and providing the advantages hereinbefore stated, it is to be understood that it is merely illustrative of the presently preferred embodiment of the invention, and that no limitations are intended to the detail of construction or design herein shown for these dental drill components other than as defined in the one or more appended claims.

What is claimed is:

1. A method of obviating the transmission to a patient of the HIV virus resulting in AIDS during a dental tooth-drilling procedure using as drilling components a dental drill burr support of a type attached to a dental drill, a burr ejection tool for said dental drill burr support, and a selected drill burr, comprising the steps of acquiring by said patient possession of said dental drill burr support, said burr ejection tool, and said selected drill burr, relinquishing said possession of said dental drill burr support, said burr ejection tool, and said selected drill burr by said patient to a dentist for use in said dental tooth-drilling procedure, attaching said dental drill burr support, said burr ejection tool, and said selected drill burr by said dentist in drilling relation to a dental drill, completing said tooth-drilling procedure and afterwards returning for subsequent use to said patient said dental drill burr support, said burr ejection tool and said selected drill burr, whereby there is exclusive use to said patient of said dental drill burr support, said burr ejection tool, and said selected drill burr to thereby obviate any contamination thereof by another patient which might transmit an AIDS infection.

* * * * *